United States Patent
Kim et al.

(10) Patent No.: US 8,765,641 B2
(45) Date of Patent: Jul. 1, 2014

(54) CHIP PRODUCTION, HYBRIDIZATION AND DATA INTERPRETATION FOR ANTIBODY AND PROTEIN MICROARRAYS

(75) Inventors: Hyesook Kim, Bloomfield Hills, MI (US); Alan A. Dombkowski, Canton, MI (US); Raymond F. Novak, Orchard Lake, MI (US); Brian B. Haab, Jenison, MI (US)

(73) Assignee: Detroit R&D, Inc., Detroit, MI (US)

( * ) Notice: Subject to any disclaimer, the term of this patent is extended or adjusted under 35 U.S.C. 154(b) by 1063 days.

(21) Appl. No.: 10/593,412

(22) PCT Filed: Mar. 18, 2005

(86) PCT No.: PCT/US2005/008973
§ 371 (c)(1),
(2), (4) Date: Sep. 18, 2006

(87) PCT Pub. No.: WO2005/090546
PCT Pub. Date: Sep. 29, 2005

(65) Prior Publication Data
US 2008/0058215 A1    Mar. 6, 2008

Related U.S. Application Data

(60) Provisional application No. 60/554,538, filed on Mar. 19, 2004.

(51) Int. Cl.
*C40B 30/04* (2006.01)
*G01N 33/563* (2006.01)

(52) U.S. Cl.
USPC .............................. 506/9; 436/513

(58) Field of Classification Search
USPC .............................. 506/9; 436/513
See application file for complete search history.

(56) References Cited

U.S. PATENT DOCUMENTS 7,232,672 B2 * 6/2007 Weiner et al. ............... 435/189

OTHER PUBLICATIONS

Haab et al., 2001, Protein microarrays for highly parallel detection and quantification of specific proteins and antibodies in complex solutions, Genome Biology, 2(2): 1-13.*
Haab, Methods and applications of antibody microarrays in cancer research, Proteomics, 3: 2116-2122, Nov. 2003.*
Nielsen et al., Profiling receptor tyrosine kinase activation by using Ab microarrays, PNAS, 100(16): 9330-9335, Aug. 5, 2003.*
Haab, B. et al., "Protein microarrays for highly parallel detection and quantitation of specific proteins and antibodies in complex solutions," *Genome Biol.* 2, Research 0004.1-0004.12 (2001).
Leukling, A. et al., "Protein microarrays for gene expression and antibody screening," *Anal. Biochem.*, 270, 103-111 (1999).
MacBeath, G., et al., "Printing proteins as microarrays for high-throughput function determination," *Science* 289, 1760-1763 (2000).
Miller, J.C. et al., "Antibody microarray profiling of human prostate cancer sera: Antibody screening and identification of potential biomarkers," *Proteomics* 3, 56-63 (2003).
Streekumar, A. et al., "Profiling of cancer cells using protein microarrays: Discovery of novel radiation-regulated proteins," *Cancer Res.* 61, 7585-7593 (2001).
Zhou, H. et al., "Two color, rolling circle amplification on antibody microarrays for sensitive, multiplexed serum protein measurements," *Genome Biology*, 5:R28 (2004).

* cited by examiner

*Primary Examiner* — Amber D Steele
(74) *Attorney, Agent, or Firm* — Kohn & Associates, PLLC

(57) ABSTRACT

An antibody microarray screen including a substrate, monoclonal and polyclonal antibodies that are purified immunoglobins, wherein the antibodies are spotted on predetermined positions on the substrate, and fluids unprocessed for immunoglobulin isolation (e.g., anti-sera, ascites fluids, or hybridoma culture media), wherein the unprocessed fluids are spotted on the predetermined positions on the substrate. Production of drug-metabolizing enzyme antibody microarrays containing closely related cytochromes P450 is disclosed. Methods of manufacturing an antibody microarray, an internal control molecule for use in an antibody microarray, a method of determining optimal spotting concentrations of IgG and a method to increase a detectable signal with microarray analysis are disclosed.

10 Claims, 3 Drawing Sheets

| | Quality Control | Experiment |
|---|---|---|
| Cy3(green): | Anti-Rabbit | Control |
| Cy5(red): | Anti-Mouse | Rat Liver after PB Treatment |

CHIP PRODUCTION, HYBRIDIZATION AND DATA INTERPRETATION FOR ANTIBODY AND PROTEIN MICROARRAYS

CROSS-REFERENCE TO RELATED APPLICATIONS

This is a National Phase Filing Under 35 U.S.C. 371, of International Application No. PCT/US05/08973, filed Mar. 18, 2005, which claims the benefit of priority of U.S. Provisional Patent Application Ser. No. 60/554,538, filed Mar. 19, 2004, both of which are incorporated herein by reference.

GOVERNMENT SUPPORT

Research in this application was supported in part by a contract from National Institute of Environmental Health Sciences (N43ES 35506). The government has certain rights in the invention.

BACKGROUND OF THE INVENTION

1. Technical Field

The present invention generally relates to array based assays and specifically to microarrays for identifying, quantifying, and qualifying target molecules.

2. Background Art

In determining the expression or function of any molecule, traditional methods in molecular biology are only useful at examining the effect of one agent on one cellular molecule, in one experiment, which means that examining any effect on any given molecule, in general, is slow, expensive and difficult to assess. The advent of microarray technology has allowed scientists to examine the effect of one treatment, condition, or combinations thereof on thousands of molecules simultaneously.

Generally, microarray technology consists of probe molecules being attached to a solid substrate and target molecules obtained from the exposed cells contacting the probe molecules. Typically, target molecules are labeled prior to exposure to the microarray. Once exposed to the microarray, some target molecules selectively form probe/target pairs by binding/hybridizing with the complimentary probe molecules on the microarray. The target molecules that do not form pairs are removed from the microarray. Where the probe/target pairs are formed on the microarray, the scientist can then visualize the probe molecules, which were bound by labeled target molecules. The relative amount of probe/target pairs that form can be compared between groups of cells, which are exposed to different treatments and cells that are not (controls) to determine the effect of the treatment. For example, the levels of expression of mRNA or protein as a target molecule may have changed, or alternatively, the conformation of a protein or carbohydrate could have changed. As thousands of molecules can be screened simultaneously using this technology, microarrays can be used to improve timeliness, effectiveness, accuracy and overall benefit-to-cost ratio for examining changes in molecular expression and function relative to traditional methods.

Biochemical molecules on microarrays have been synthesized directly at or on a particular cell (sector) on the microarray, or preformed molecules have been attached to particular cells (sectors) of the microarray by chemical coupling, adsorption or other means. The number of different cells (sectors) and therefore the number of different biochemical molecules being tested simultaneously on one or more microarrays can range into the thousands. Commercial microarray plate readers typically measure fluorescence in each cell (sector) and can provide data on thousands of reactions simultaneously thereby saving time and labor. A representative example of a patent in the field is U.S. Pat. No. 5,545,531.

Currently, two dimensional arrays of macromolecules are made either by depositing small aliquots on flat surfaces under conditions which allow the macromolecules to bind or be bound to the surface, or the macromolecules can be synthesized on the surface using light-activated or other synthetic reactions. Previous methods also include using printing techniques to produce such arrays. Some methods for producing arrays have been described in "Gene-Expression Micro-Arrays: A New Tool for Genomics", Shalon, D., in Functional Genomics; Drug Discovery from Gene to Screen, IBC Library Series, Gilbert, S. R. & Savage, L. M., eds., International Business Communications, Inc., Southboro, Mass., 1997, pp 2.3.1.-2.3.8; "DNA Probe Arrays: Accessing Genetic Diversity", Lipshutz, R. J., in Gilbert, S. R. & Savage, L. M., supra, pp 2.4.1.-2.4.16; "Applications of High-Throughput Cloning of Secreted Proteins and High-Density Oligonucleotide Arrays to Functional Genomics", Langer-Safer, P. R., in Gilbert, S. R. & Savage, L. M., supra; Jordan, B. R., "Large-scale expression measurement by hybridization methods: from high-densities to "DNA chips", J. Biochem. (Tokyo) 124: 251-8, 1998; Hacia, J. G., Brody, L. C. & Collins, F. S., "Applications of DNA chips for genomic analysis", Mol. Psychiatry 3: 483-92, 1998; and Southern, E. M., "DNA chips: Analyzing sequence by hybridization to oligonucleotides on a large scale", Trends in Genetics 12: 110-5, 1996.

One difficulty in microarray technology has been the ability of scientists to efficiently and effectively identify and quantify the probe/target pairs which form on the microarray. As above, the target molecule is typically labeled and that label is detected to identify the probe/target pair. However, the label may not be present on the target molecule in sufficient amounts to be detectable. If a target sequence is not adequately labeled, false negative results are obtained, meaning that probe/target pairs are formed, but not identified by the scientist. Labeling inadequacies often occur due to enzymatic reproducibility, inhibition and or incomplete incorporation of dyes.

Recently, protein and antibody microarrays have been developed using a robotic system used for DNA microarrays (Haab, et al., 2001, Leukling, et al., 1999, MacBeath and Schreiber, 2000, Streekumar, et al., 2001, and Miller, et al., 2003). Scanners and software required to visualize and quantitate fluorescence signals and bioinformatic tools for data mining of DNA arrays can be used for antibody microarray analysis. Moreover, data mining of antibody microarray analyses are almost identical to the DNA arrays. However, development of functional, focused (non-global) antibody arrays is challenging because of a limited number of antibodies that are available for microarray chip production and form-specific antibodies of interest differ greatly in their binding strength to the antigen.

The Lueking et al. (1999) reference disclosed the spotting of 92 crude cell lysates obtained from *E. coli* transfected with human fetal brain cDNA-containing vectors on the polyvinylidine difluoride (PVDF) membrane. The spotted proteins were hybridized with monoclonal antibodies followed by hybridization with secondary antibodies conjugated with horseradish peroxidase (HRP). Peroxidase activity of the secondary antibody conjugates was detected by incubation of the membrane with CN/DAB solution (Pierce). Meanwhile, the MacBeath and Schreiber (2000) reference disclosed production of microarray slides by conjugating proteins with BSA-N-hydroxysuccinimide coated on glass slides. Using the technology, arrays for three pairs of proteins that were known to interact, three pairs of kinase-substrate proteins, and three pairs of small molecules-binding proteins were produced and the utility of the arrays was explored.

The Haab et al. (2001) reference disclosed production of both protein and antibody microarrays with 115 antigen and antibody (IgG) pairs. Antigen proteins or antibodies were spotted on poly-L-lysine coated glass with a cross-linking layer. Concentration of the antigen proteins or antibodies spotted on the slides was limited to any single concentration between 0.1 and 0.3 mg/ml. Contrary to the single concentration of the antigen proteins or antibodies spotted on the slide, six different concentrations of antigen proteins or antibodies were conjugated with dyes and hybridized with the spotted antigen proteins or antibodies to test sensitivity. It was found that 50% of the arrayed antigen proteins and 20% of the arrayed antibodies provided meaningful data at or below concentrations of 0.34 µg/ml and 1.6 µg/ml, respectively.

The Sreekumar et al. (2001) reference disclosed the production of antibody microarrays with poly-L-lysine coated or superaldehyde-modified glass slides (Telechem International Inc., Sunnyvale, Calif.). This was a targeted microarray of 146 antibodies for stress response, cell cycle progression, and apoptosis spotted with single concentration of antibodies.

Finally, the Miller et al. (2003) reference disclosed the spotting of 184 monoclonal and polyclonal immunoglobulin (IgG) on poly-L-lysine (CEL Associates, Pearland, Tex.) with a photoreactive cross-linking layer (Molecular Biosciences, Boulder, Colo.) or polyacrylamide-based hydrogel (Packard Bioscience, Meriden, Conn.) glass slides. Concentration of the antibodies spotted on the slide was limited to any single concentration between 0.1 and 0.3 mg/ml. This was a targeted antibody array used for serum prostate cancer marker screening. Thus, 40 antibodies for serum proteins detected in the serum of normal person and 13 antibodies for proteins detected in the serum of cancer patients were included.

In view of the prior art, no antibody microarrays have been developed for anti-sera or ascites fluids. Accordingly, the present invention relates to spotting increased levels of anti-sera or ascites fluids to compensate for proteins other than IgG in the anti-sera or ascites fluids, which made it possible to include additional form-specific antibodies. Contrary to DNA microarrays produced to detect global gene expression, it is impossible to produce antibody microarrays to detect global protein expression primarily due to small number (lower than 500) of antibodies spotted on the chip. Thus, bias of data resulted from the unique set of the antibodies spotted on the arrays has to be corrected with a spiked internal control, which is not expressed in the samples. Use of the internal control for normalization of the target arrays has not been previously reported. So far, single concentration of IgG has been spotted for array analysis. In the present invention, a method to determine optimal IgG levels to obtain optimal signal levels in microarrays by spotting various concentrations of IgG is disclosed. In the present invention, the advantage of spotting various concentrations of IgG is also disclosed.

Drug metabolizing enzyme antibody microarrays were produced using purified immunoglobulins (IgG) as well as fluids unprocessed for IgG isolation, e.g., anti-sera or ascites fluids. They were used to analyze protein expression of hepatic proteins obtained after phenobarbital treatment of rats. Twelve up-regulated proteins after phenobarbital treatment were identified by the antibody microarray. It was surprising that, in Western blot analysis, only 1 out of the 12 up-regulated proteins failed to show increased protein expression.

SUMMARY OF THE INVENTION

The present invention provides an antibody microarray screen including a substrate, monoclonal and polyclonal antibodies that are purified immunoglobins and fluids unprocessed for immunoglobulin isolation, wherein the antibodies and fluids unprocessed for immunoglobulin isolation are spotted on the predetermined positions. Further, the present invention provides an antibody microarray screen including a substrate, polyclonal antibodies as purified immunoglobins, wherein the antibodies are spotted on predetermined positions on the substrate, and anti-sera spotted on the predetermined positions. The present invention also provides an antibody microarray screen including a substrate, monoclonal antibodies as purified immunoglobin, wherein the antibodies are spotted on predetermined positions on the substrate, ascites fluid spotted on the substrate, and hybridoma culture media spotted on the substrate. Additionally, methods of manufacturing an antibody microarray are provided. Furthermore, the present invention provides an internal control molecule for use in an antibody microarray. The present invention further provides a method of determining optimal spotting concentrations of IgG and a method to increase a detectable signal with microarray analysis.

BRIEF DESCRIPTION OF THE DRAWINGS

Other advantages of the present invention will be readily appreciated, as the same becomes better understood by reference to the following detailed description when considered in connection with the accompanying drawings wherein.

DETAILED DESCRIPTION OF THE INVENTION

Figure 1:
FIG. 1 shows quality control analysis of antibody chips using anti-mouse and anti-rabbit IgG and microarray analysis of rat hepatic proteins for phenobarbital treatment (a representative image is shown)
Figure 1:
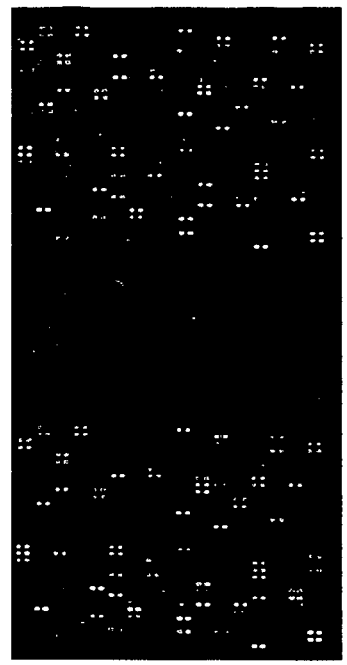

Generally, the present invention relates to a microarray including a substrate on which a plurality of sample spots is arranged in a two-dimensional array. The present invention provides a method of producing antibody drug-metabolizing enzyme antibody microarrays. Specifically, the present invention relates to microarrays including closely related cytochromes P450. The present invention also relates to producing antibody chips with fluids that are not processed for immunoglobulin isolation including anti-sera, ascites fluids, and hybridoma culture media. The present invention relates to analysis of levels of spotted IgG by hybridization of labeled secondary IgG to decide optimal antibody levels to spot on the slide. Use of a spiked internal control to normalize microarray data obtained from focused (non-global) array analysis is also disclosed. Further, the present invention provides a method to increase signal with array analysis using an intensive molecular signal.

The microarray of the present invention can be produced using monoclonal and polyclonal antibodies as purified immunoglobulins as well as fluids that are not processed for immunoglobulin isolation, including anti-sera, ascites fluids and hybridoma culture media. According to the present invention a method is disclosed to increase signal strength of array analysis utilizing intensive molecular signals. Further, the present invention relates to production of drug-metabolizing enzyme antibody microarrays. The present invention also provides a method of producing drug-metabolizing enzyme antibody microarrays including closely related cytochromes P450.

The present invention is useful in toxicoproteomics. Specifically, the present invention can be used in the identification, quantification, and qualification of protein products. Further the present invention is useful in analyzing numerous samples simultaneously. Automated chip construction, use of fluorescent signals, and custom digital image analysis make it possible to monitor expression of hundreds of proteins and to obtain expression profiles of environmental toxins. Additionally, the present invention can predict optimal ranges of antibody spotting levels by hybridization of the antibodies on the slide with secondary antibodies with known signal strength. The present invention can be used to analyze levels of spotted IgG by hybridization of labeled secondary IgG to determine optimal antibody levels to spot on the slide.

As used herein, the term "spotting" is defined as a method of arranging a plurality of sample spots on a two-dimensional array. The sample spots have a predetermined positional relationship as is well known to those of skill in the art.

As used herein, the term "substrate" is defined as any solid support including, but not limited to, silicon, plastic, glass, ceramic, rubber, polymer, a composite thereof, and any other similar substrate known to those of skill in the art.

As used herein, the term "predetermined positions" is defined as a plurality of positions or locations on the substrate, wherein each individual position is sufficiently separated from each other so that, if needed, compounds, antibodies, samples, reagents, etc. can be added and/or withdrawn and reactions can be conducted in one position independently from another position. Thus, the predetermined position can have a single or numerous substances, compounds, antibodies, samples, reagents, combined in the position therein.

The present invention has numerous embodiments. In one embodiment, the present invention provides an antibody microarray screen including a substrate, monoclonal and polyclonal antibodies that are purified immunoglobins, and fluids unprocessed for immunoglobulin isolation. The antibodies and fluids are spotted on predetermined positions on the substrate. The antibodies detect numerous proteins. For example, drug-metabolizing enzymes such as cytochromes P450, proteins functionally related with the drug-metabolizing enzymes such as mitochondrial proteins, apoptosis-related proteins, anti-oxidant proteins, oxidative stress proteins, and intracellular protein degradation proteins, and other similar proteins known to those of skill in the art can all be used with the microarray of the present invention. Further, the substrate can include a hydrogel (polyarylamide-based) coating. The screen can optionally include labeled secondary immunoglobulins, wherein the secondary immunoglobulin levels are analyzed. Finally, the screen includes fluids such as, but not limited to, ascites fluids, hybridoma culture medium, anti-sera, and the like.

In this embodiment of the present invention, there is provided a drug-metabolizing enzyme antibody microarray. There are Phase I and II drug-metabolizing enzymes. Cytochromes P450 (CYPs), Phase I enzymes with closely related subfamily, normally catalyze the first step of xenobiotic metabolism with a required co-enzyme, CYP-NADPH reductase or cytochrome $b_5$. Glutathione S-transferases, sulfotransferases, epoxide hydrolases, N-acetyl transferases, and UDP-glucusonyl transferases are Phase II enzymes in drug metabolism.

CYPs with diverse substrate specificity and metabolism play an active role in the metabolism of numerous physiological substrates such as steroid hormones, fatty acids, prostaglandins, and bile acids as well as countless xenobiotics including drugs, chemical carcinogens, insecticides, petroleum products, and other environmental pollutants. The drug metabolizing enzymes induce oxidative stress, and other known processes known to those of skill in the art.

Antibody chips were produced by spotting antibodies (approximately 30 monoclonal and approximately 50 polyclonal antibodies) for Phase I and II drug-metabolizing enzymes and proteins functionally related with drug-metabolizing enzyme including mitochondrial proteins involved with apoptosis and oxidative stress, apoptosis-related proteins, anti-oxidant proteins, oxidative stress proteins and intracellular protein degradation proteins (See Table 1). Previously, no antibody microarrays targeted for drug metabolizing enzymes and functionally related proteins were produced. This array was not for analysis of expression of global protein collection. Thus, it was necessary to spike an internal control prior to probe conjugation to be used for data normalization. The fact that the normalization factors obtained by spiking the Flag protein internal control were 1.0 and 0.97 at 500 and 50 µg/ml IgG, respectively, with the focused (non-global) array was surprising considering that phenobarbital treatment markedly increased a few CYPs. The drug metabolizing enzyme array containing CYPs proteins and proteins functionally related with drug-metabolizing enzyme, including mitochondrial proteins involved with apoptosis and oxidative stress, apoptosis-related proteins, anti-oxidant proteins, oxidative stress proteins and intracellular protein degradation proteins, is a focused array, but behaves as if it is a global array due to a result of containing correct groups of proteins.

In another embodiment of the present invention, there is provided an antibody microarray screen including a substrate; polyclonal antibodies as purified immunoglobins, and anti-sera. The screen can detect various proteins, including, but not limited to, drug-metabolizing enzymes, cytochromes P450, proteins functionally related with the drug-metabolizing enzymes such as mitochondrial proteins, apoptosis-related proteins, anti-oxidant proteins, oxidative stress proteins, and intracellular protein degradation proteins, and other similar proteins known to those of skill in the art. Furthermore, the screen can include a hydrogel (polyarylamide) coating. Finally, the screen can optionally include labeled secondary immunoglobins.

In another embodiment of the present invention, there is provided an antibody microarray screen including a substrate; monoclonal antibodies as purified immunoglobin; ascites fluid spotted on the substrate; and hybridoma culture media spotted on the substrate. Again, any protein as set forth above can be detected with this microarray screen. Additionally, the screen can include a hydrogel (polyarylamide) coating and can include labeled secondary immunoglobins.

In another embodiment of the present invention, antibody solutions with increasing concentration of 0 (PBS), 0.5, 5, 50 and 500 μg/ml were spotted on both hydrogel- and nitrocellulose-based antibody chips. Additional chips were produced by spotting 500 and 1000 μg IgG on both the hydrogel and nitrocellulose-based chips.

Both hydrogel and nitrocellulose-based slides showed satisfactory cross-reactivity with the secondary IgG. However, when the slides were hybridized with protein probes, only hydrogel slides produced meaningful results with low background. The results demonstrate that, whereas secondary IgG recognized antibodies spotted on the both surface materials very efficiently, antibodies spotted on the hydrogel recognized protein probes better than antibodies spotted on the nitrocellulose membrane. Thus, antibodies spotted on the hydrogel maintained their original molecular structure, which is necessary for recognition of probes during hybridization.

In a further embodiment of the present invention, polyclonal IgG, anti-sera and monoclonal antibodies purified or as ascites fluids were used to produce a drug metabolizing enzyme antibody microarray (Table 1). The fluids used for slide spotting without immunoglobulin fraction purification were 10-fold diluted to achieve array results similar to 0.5 mg/ml IgG. Protein levels of four polyclonal anti-sera ranged from 38 to 75 mg/ml. Thus, when anti-sera or ascites fluids were spotted, higher amount of protein compared with purified IgG protein has to be spotted to compensate non-IgG proteins in the fluids.

A method to analyze quality of the array spots has been developed with the present invention. The antibody slide was hybridized with labeled secondary IgG, e.g. 25 μg Cy3-conjugated anti-rabbit IgG mixed with 50 μg Cy5-conjugated anti-mouse IgG, followed by scanning of the chip to compare signal strength of each spot and to assess evenness of each spot (Table 2).

Signal levels obtained from spotting 100-fold and 10-fold diluted anti-sera or ascites fluids were similar to the spots obtained with 50 and 500 μg/ml IgG spotting, respectively. This result demonstrated that estimation of IgG levels of the anti-sera and ascites fluids was correct. Polyclonal antibodies for CYP3A were spotted for array analysis as anti-serum without isolation of IgG. CYP3A was previously reported to increase after phenobarbital treatment. Array analysis revealed that CYP3A expression increased higher than two-fold after phenobarbital treatment (Table 3). Six mouse ascites fluids including antibodies for tubulin-alpha demonstrated a 1.7-fold increase after phenobarbital treatment, while alpha-actin (0.8-fold of control, 20% decrease) and beta-actin (1.6-fold increase) were also successfully used for antibody array production (Tables 1 and 4). The results demonstrated that anti-sera or ascites fluids (without IgG purification, thus containing high levels of proteins) could be spotted on the chip to achieve a successful antibody microarray analysis.

Antibody concentration-dependent signal strength can be obtained by hybridization of secondary IgG utilizing the present invention. Antibodies for the microarray were spotted in four blocks (two spots in each concentration) on top of the slide and the four blocks were repeated on the bottom of the slide. Quality control analysis was carried out using labeled secondary antibodies hybridized with the antibody chips (FIG. 1, "Quality Control"). Majority of the spots visible in the quality control analysis were round and bright red (monoclonal IgG) or green (polyclonal IgG) with low background signal. Spots in block one (144 spots) were used to count % visible spot counting in each concentration of IgG and shown in Table 2. All spots of 500 μg/ml IgG showed strong signal, 11% and 72% of spots from 50 μg/ml and 5 mg/ml IgG, respectively, failed to show. None of the 0.5 mg/ml IgG spot showed any signal. The result demonstrated that the quality control spot signal strength of each spot was IgG concentration-dependent. Thus, the quality control analysis can be used for selection of optimal IgG concentration for array production.

In another embodiment of the present invention, there is provided an internal control used for normalization of focused (non-global) array data. Each IgG concentration (0.5, 5, 50 and 500 μg/ml) has sixteen data points. There are two data points for the top block and two bottom blocks (four data points). With dye swap, there are eight data points. In total, there are sixteen data points from eight data points from Control 1/PB 1 and eight data points from Control 2/PB 2.

Anti-Flag IgG, which recognizes Flag protein, an internal control protein for Cy3 and Cy5 conjugation and hybridization, was spotted three times in each block (top and bottom blocks). Prior to Cy3 and Cy5 conjugation, 2 μg of the Flag landmark protein was spiked to 1 mg of protein. After hybridization of the chips with the probe, signal strength of each spot was obtained. Ratios of signal strength of Flag protein spiked in control and protein obtained from phenobarbital treated rats were 9.7 (mean of 1.2, 0.9, and 0.8) and 1.0 (mean of 1.1, 1.1 and 0.9) for 50 and 500 μg/ml IgG spots, respectively (Table. 3). The mean ratio was used as a normalization factor (NF) for the array analysis.

The Flag internal controls in 500 μg/ml IgG array analysis did not change after phenobarbital treatment. Contrary to the hypothesis that house-keeping proteins do not change after chemical treatment, protein expression of tublin-alpha and beta-actin changed 1.7- and 1.6-fold (70% and 60% increase, respectively), respectively, after phenobarbital treatment. Expression level of alpha-actin and tubulin-beta changed to 0.8 and 0.7 of internal control (20% and 30% decrease, respectively). The only housekeeping protein that did not change after phenobarbital treatment was G3PDH (1.0 of internal control). There was a 60% increase of protein expression level of beta-actin, which is widely used as an internal control for Western blot analysis. With use of the Flag internal control, it has been found that G3PDH was the only housekeeping protein suitable for an internal control of Western blot analysis (Table 4). Thus, suitability of G3PDH to be used as an internal control for this specific array analysis was confirmed only through use of a Flag internal control. Targeted, focused microarray data, which were not obtained from array analysis of global, comprehensive collection of genes or proteins, have to be normalized using a normalization factor obtained from an internal control spiked to the array samples prior to probe conjugation. Using housekeeping gene or protein expression can mislead data interpretation.

In another embodiment of the present invention, there is provided a method of spotting more than a single concentration of antibodies. More specifically, the method determines optimal spotting concentrations of IgG by spotting increasing concentrations of IgG on microarray slides; hybridizing the slides with secondary IgG with a detectable signal; and scanning and quantitating signal strength of each spot and selecting optimal concentrations of IgG. Out of 312 (78 antibodies×4 concentrations) consolidated protein data points (76 proteins+2 additional Flag proteins with 4 various concentration of antibodies), 12 consolidated protein data points showed up-regulated expression levels which were the same or higher than 2-fold after phenobarbital (PB) treatment (Table 3).

The twelve proteins were up-regulated higher than 2-fold. There were two proteins at 5 µg/ml, five proteins at 50 µg/ml IgG spots and five proteins at 500 µg/ml IgG spots. No proteins showed any up-regulated expression after phenobarbital treatment with 0.5 µg/ml IgG spots. This is primarily due to extremely low spotting levels of the proteins. A quality control using secondary IgG revealed that the 0.5 µg/ml spots were under the detection limit (Table 2). This result showed that spotting antibodies more than a single concentration was beneficial because it compensated differential expression levels of proteins.

Figure 2:
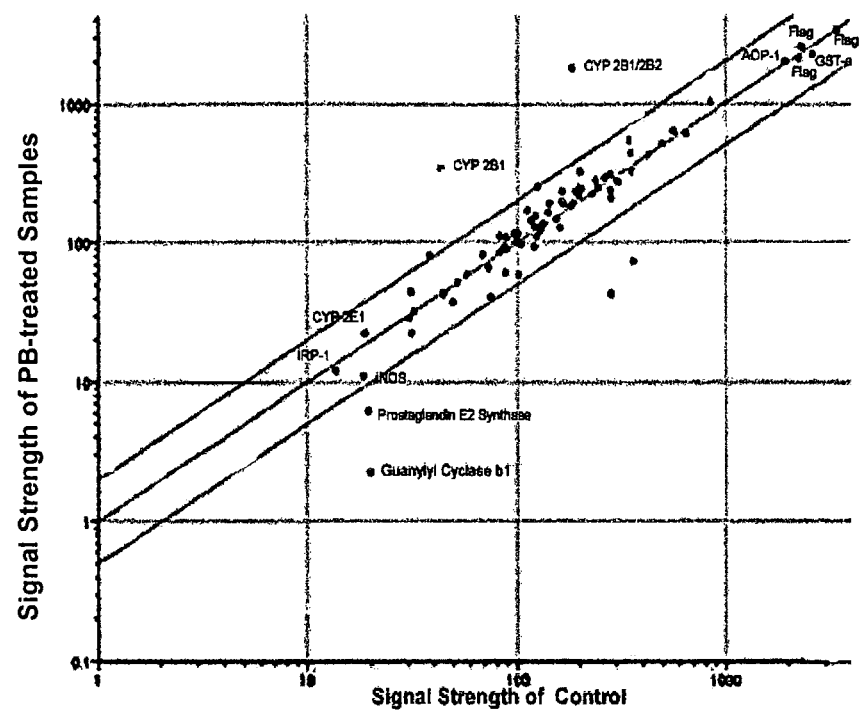
FIG. 2 illustrates expression levels of rat hepatic proteins obtained from untreated rats and rats treated with phenobarbital, wherein consolidated data from four microarray analyses were obtained with 500 µg/ml antibody spotting (16 data points per spot)

In order to further demonstrate the effectiveness of the present invention, Gene Spring™ analysis of 500 µg/ml antibody spots is shown in FIG. 2. The middle diagonal line is for a protein expression level that did not change after PB treatment, the top line is for 2-fold increase, and the bottom line is for 2-fold decrease. Internal control, Flag proteins (3 sets) (2 µg), spiked to 1 mg of sample, were close to the middle line as expected and showed high signal values (mean value, 2663). GST-alpha and antioxidant-like protein 1 also showed high expression levels without any change. CYP2B1 and CYP2B1/2B2 spots were above the 2-fold increase line with 9.3- and 9.7-fold increase, respectively, after PB treatment. CYP2B1 was reported to be a primary protein that increased after PB treatment. An interesting observation is that both CYP2B1 IgG and CYP2B1/2B2 IgG bound with CYP2B1 protein.

Majority of the spots after normalization with Flag internal control (this case, the normalization factor was 1, which means no change) were close for the middle diagonal line. Spotting high level (500 µg/ml) of IgG, especially high protein spotting with anti-sera and ascites fluids to achieve the same levels of IgG, produced an array result of signal strength of the spots with 10 or higher as shown in FIG. 2.

Verification of microarray results also occurred. Protein levels of CYP2B1/2B2, CYP2B1, CYP3A, COX-2 and CYP2D6 increased after PB treatment obtained by 500 µg/ml IgG spots (Table 3, FIG. 2) were verified by Western blot analyses of microsomal and cytosolic proteins (Table 5). Levels of microsomal proteins were normalized by microsomal CYP2C11 levels, which do not change after PB treatment, using hepatic microsomal proteins obtained from untreated or phenobarbital-treated rats. Cytosolic COX-2 levels were normalized by G3PDH levels.

Comparison of up-regulated expression levels of each protein obtained by array analyses with Western blot analysis is shown in Table 5. There was agreement in results obtained by the arrays with Western blot analyses except for the CYP2D expression level, which increased after phenobarbital treatment by array analysis but failed to increase by Western blot analysis.

The present invention also provides a method of manufacturing an antibody microarray by spotting more than a single concentration of antibodies on a microarray substrate to increase the number of up-regulated protein detection. The method also includes an antibody concentration that is more than 5 µg/ml IgG.

The present invention also provides an internal control molecule for use in an antibody microarray, wherein the internal control molecule is not expressed in the array sample for normalization of focused (non-global) array data. The internal control molecule can be, but is not limited to, a Flag protein and a non-mammalian protein. The internal control molecule is used to compare the expression ratio of housekeeping proteins to select a housekeeping genes by determining if any difference exists between the control and experimental samples.

The present invention also provides a method to increase a detectable signal with microarray analysis by utilizing an intensive molecular signal, which is produced by conjugation of a dye or a reporter molecule to a protein in that interference of the IgG binding to a protein is created. The intensive molecular signal is produced by conjugation of a dye and a reporter molecule to a protein to the extent that interference of Coomassie blue stain binding to the protein is created. The intensive molecular signal is used for antibody microarrays or for protein microarrays. Further, the present invention provides a method to increase a detectable signal with microarray analysis by conjugating a dye and a reporter molecule to a protein; and creating interference of an IgG molecule binding to the protein.

Figure 3:
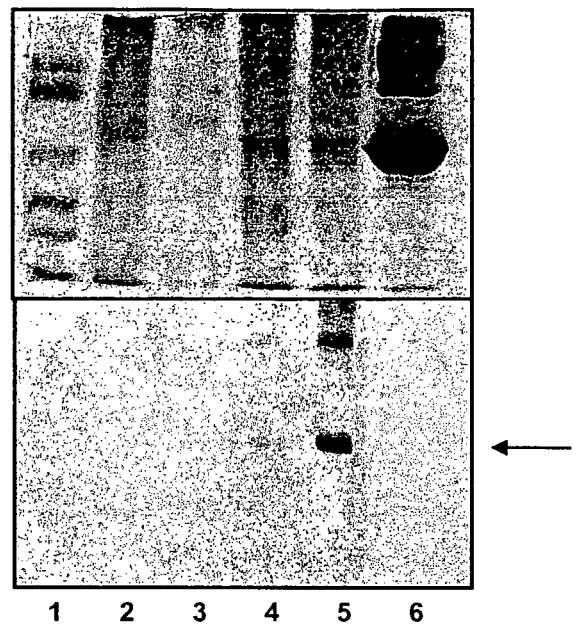
FIG. 3 demonstrates Cy3- and Cy5-conjugated microsomal proteins, specifically, Coomassie blue staining (top) and Western blot analysis with anti-mEH (bottom), wherein lane 1 has pre-stained standards, lanes 2 and 4 have 10 µg hepatic microsomal proteins from control rats, lanes 3 and 5 have 10 µg hepatic microsomal proteins from phenobarbital treated rats, lane 6 has Cy5-conjugated anti-mouse IgG (Biomeda Co.), and lanes 2 and 3 have Cy3- and Cy5-conjugated microsomal proteins (Cy3 is green in fluorescence but pink in the visible light and Cy5 is red in fluorescence but bluish green in the visible light).

The methods set forth above are conjugation methods wherein antibody binding to a protein was inhibited by conjugated dye molecules. Inhibition of the antibody recognition of the labeled microsomal epoxide hydrolase was determined by Western blot analysis (FIG. 3, bottom). This is due to interference of the dye molecule bound to the epitope of the protein recognized by the IgG. This intensive labeling method cannot be used for Cy3 and Cy5 conjugation for sample proteins in direct array analysis and streptavidin or anti-digoxigenin in indirect array analysis because the molecules have to be recognized by IgG or have to recognize biotin- or digoxigenin-conjugated proteins, respectively. However, the method can be utilized to attach the intensely labeled proteins (Intense Molecular Signals) via carboxyl groups of the molecules to proteins or streptavidin or anti-digoxigenin in direct and indirect array analyses, respectively.

In the specific example of dye conjugation using Cy3 or Cy5, majority of $NH_2$ and $NH_3^+$ groups present in a mixture of proteins were occupied with Cy3 and Cy5 molecules as evidenced by PAGE analysis followed by Coomassie blue staining. Cy5-conjugated anti-mouse IgG (low level of Cy5 molecules were conjugated so that the majority amino groups were available for Coomassie blue staining) and proteins that were not conjugated with the dye stained in blue whereas Cy3- and Cy5-conjugated proteins showed pink-(visible color of Cy3) and bluish green (visible color of Cy5)-colored bands (FIG. 3, top).

The proteins were not heat- or chemically denatured prior to dye conjugation, but simply dissolved in 0.1 M sodium carbonate buffer. Under the non-denaturing condition, conjugation of dye molecules is limited to amino groups exposed to the surface of the protein leaving internally located amino groups intact. Thus, it was unexpected finding that all the amino groups of the proteins were labeled with this method without heat- or chemical denaturation of the proteins prior to dye conjugation.

Finally, the present invention provides a method of producing antibody microarrays by spotting antibodies for Phase I and II drug metabolizing enzymes and proteins functionally related with the drug-metabolizing enzymes. The proteins include, but are not limited to, mitochondrial proteins, apoptosis-related proteins, anti-oxidant proteins, oxidative stress proteins, and intracellular protein degradation proteins. Further, the targeted drug-metabolizing enzyme antibody microarray includes an internal control to be used for data normalization, wherein the internal control is a Flag protein.

The above discussion provides a factual basis for the method of the present invention for production and use of antibody, and/or focused (non-global) microarray. The methods used with and the utility of the present invention can be shown by the following non-limiting examples and accompanying figures.

EXAMPLES

Materials and Methods

General Methods in Immunology:

Standard methods in immunology known in the art and not specifically described are generally followed as in Stites et al. (eds), Basic and Clinical Immunology (8th Edition), Appleton & Lange, Norwalk, Conn. (1994) and Mishell and Shiigi (eds), Selected Methods in Cellular Immunology, W.H. Freeman and Co., New York (1980).

Immunoassays:

In general, ELISAs are the preferred immunoassays employed to assess a specimen. ELISA assays are well known to those skilled in the art. Both polyclonal and monoclonal antibodies can be used in the assays. Where appropriate other immunoassays, such as radioimmunoassays (RIA) can be used as are known to those in the art. Available immunoassays are extensively described in the patent and scientific literature. See, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521 as well as Sambrook et al, Molecular Cloning: A Laboratory Manual, Cold Springs Harbor, N.Y., 1989

Western Blot Analysis:

Western blot analysis as well as co-immunoprecipitation employed to assess levels of expression and to demonstrate association of two proteins in Ausubel et al., Current Protocols in Molecular Biology, John Wiley and Sons, Baltimore, Md. (1989, 2002).

Antibody Production:

Antibodies can be monoclonal, polyclonal or recombinant. Conveniently, the antibodies can be prepared against the immunogen or portion thereof for example a synthetic peptide based on the sequence, or prepared recombinantly by cloning techniques or the natural gene product and/or portions thereof can be isolated and used as the immunogen. Immunogens can be used to produce antibodies by standard antibody production technology well known to those skilled in the art as described generally in Harlow and Lane, Antibodies: A Laboratory Manual, Cold Spring Harbor Laboratory, Cold Spring Harbor, N.Y., 1988 and Borrebaeck, Antibody Engineering—A Practical Guide, W.H. Freeman and Co., 1992. Antibody fragments can also be prepared from the antibodies and include Fab, F(ab')2, and Fv by methods known to those skilled in the art.

For producing polyclonal antibodies a host, such as a rabbit or goat, is immunized with the immunogen or immunogen fragment, generally with an adjuvant and, if necessary, coupled to a carrier; antibodies to the immunogen are collected from the sera. Further, the polyclonal antibody can be absorbed such that it is monospecific. That is, the sera can be absorbed against related immunogens so that no cross-reactive antibodies remain in the sera rendering it monospecific.

For producing monoclonal antibodies, the technique involves hyperimmunization of an appropriate donor with the immunogen, generally a mouse, and isolation of splenic antibody producing cells. These cells are fused to a cell having immortality, such as a myeloma cell, to provide a fused cell hybrid, which has immortality and secretes the required antibody. The cells are then cultured, in bulk, and the monoclonal antibodies harvested from the culture media for use.

For producing recombinant antibody (see generally Huston et al, 1991; Johnson and Bird, 1991; Mernaugh and Mernaugh, 1995), messenger RNAs from antibody producing B-lymphocytes of animals, or hybridoma are reverse-transcribed to obtain complimentary DNAs (cDNAs). Antibody cDNA, which can be full or partial length, is amplified and cloned into a phage or a plasmid. The cDNA can be a partial length of heavy and light chain cDNA, separated or connected by a linker. The antibody, or antibody fragment, is expressed using a suitable expression system to obtain recombinant antibody. Antibody cDNA can also be obtained by screening pertinent expression libraries.

The antibody can be bound to a solid support substrate or conjugated with a detectable moiety or be both bound and conjugated as is well known in the art. (For a general discussion of conjugation of fluorescent or enzymatic moieties see Johnstone & Thorpe, Immunochemistry in Practice, Blackwell Scientific Publications, Oxford, 1982.) The binding of antibodies to a solid support substrate is also well known in the art. (see for a general discussion Harlow & Lane Antibodies: A Laboratory Manual, Cold Spring Harbor Laboratory Publications, New York, 1988 and Borrebaeck, Antibody Engineering—A Practical Guide, W.H. Freeman and Co., 1992) The detectable moieties contemplated with the present invention can include, but are not limited to, fluorescent, metallic, enzymatic and radioactive markers such as biotin, gold, ferritin, alkaline phosphatase, b-galactosidase, peroxidase, urease, fluorescein, rhodamine, tritium, 14C and iodination.

Polyacrylamide Chips

Polyacrylamide (hydrogel)-based chips and nitrocellulose (FAST™)-based chips were obtained from PerkinElmer Life Sciences and Schleicher & Schuell Biosciences, respectively. Cy3- or Cy5-conjugated antibodies for mouse, rabbit and goat IgGs were obtained from Biomeda Co (Foster City, Calif.). NHS-Cy3 or NHS-Cy5 was obtained from Amersham. Other reagents were obtained from Sigma Chemical Co.

Quality Control of Antibody Chips

Antibody solutions were spotted (spotting volume, 1 nl) on both polyacrylamide (hydrogel)- and nitrocellulose (FAST)-based chips using split pin technology. The chip was blocked for 45 minutes at room temperature with TTBS solution. A quality control was carried out by hybridizing the chip with 25-50 µg Cy3- or Cy5-conjugated anti-rabbit IgG, anti-mouse IgG or anti-goat IgG (total volume, 0.5 to 1 ml) for one hour at room temperature. Washing was carried out with TTBS four times. The chip was dried and imaging was carried out using GenePix 4000A.

Microarray Analyses with Dye Swaps of Two Sets of Treatment Groups

Hepatic proteins (microsomal and cytosolic proteins) from livers of male Sprague Dawley rats were dialyzed with 10 kDa molecular cut-off membrane. An internal control protein, Met-Flag fusion protein recognized by anti-Flag was added to both untreated and phenobarbital-treated samples prior to Cy3- or Cy5-conjugation. The rat proteins (0.5 mg microsomal protein+0.5 mg cytosolic protein) with Flag protein (2 µg) were mixed and cross linked with NHS-Cy3 or NHS-Cy5 dissolved in 1 mL $H_2O$ (Amersham Cat No. PA23001 and PA25001, respectively). The probes were washed three times with 500 µl PBS and concentrated to 40 µl using microconcentrator spin columns (Amicon, 10 kDa cut-off). Hybridization of the probes produced from Control 1/PB 1 set (1st treatment set) and Control 2/PB 2 set (2nd treatment set) was carried out with dye swaps (in total, 4 hybridizations, 16 data points for each 0.5, 5, 50 and 500 µg/ml IgG concentration). The hybridization solution contained 2 mg of rat liver protein (total volume, 750 µl).

After hybridization, the chips were dried and images were scanned at 532 nm (green) and 635 nm (red) and pseudo-colored images were obtained using a GenePix 4000A (Axon Instruments). Signal intensity of each target protein was quantified with GenePix software using a gal (spot design) file, which contained the identity of each protein and its location in the 384-well plate.

Consolidated data from four microarray analyses were obtained with 0.5, 5, 50 and 500 µg/ml antibody spots (16 data points per spot). Fold-increase or decrease in protein expression levels after phenobarbital treatment of rats was calculated by combining data obtained by dye swaps using GeneSpring analysis. Signal levels under 10 (an arbitrary unit by GenePix quantitation) in both control and phenobarbital treated samples were deleted.

The mean (normalization factor) of 3 Flag protein internal control data points for each IgG concentration was obtained. Data points were normalized by dividing fold-increase or decrease in protein expression levels with the normalization factor pertinent to IgG concentration.

Sodium Dodecyl Sulfate-Polyacrylamide Gel Electrophoresis (SDS-PAGE) and Western Blot Analysis SDS-PAGE was carried out on 10% or 15% gels. The separated proteins were electroblotted onto cellulose membrane and Western blot analyses were carried out using horseradish peroxidase-system with electrochemiluminescent substrates.

Intensive Molecular Signal production

Cytosolic protein (0.5 mg) and microsomal protein (0.5 mg) in 1 ml 0.1 M sodium carbonate buffer, pH 9.3, were poured into a dye vial containing powdered NHS-Cy3 or NHS-Cy5 (Amersham) and incubated at room temperature for thirty minutes. The probes were washed three times with 500 µl PBS and concentrated to 40 µl using microconcentrator spin columns (Amicon, 10 kDa cut-off).

Disappearance of dye- and antibody-binding sites of the intensively labeled proteins was tested by PAGE analysis followed by Coomassie blue staining and Western blot analysis of the proteins using antibodies for microsomal epoxide hydrolase, respectively. Anti-mouse IgG conjugated with minimal Cy-5 molecules and proteins without dye conjugation stained in blue whereas proteins intensely conjugated with Cy3 and Cy5 showed pink (visible color of Cy3) and bluish green (visible color of Cy5) bands, respectively (FIG. 3, top). Intense labeling prevented antibody recognition of microsomal epoxide hydrolase (FIG. 3, bottom).

Example 1

Rat Drug-Metabolizing Enzyme Microarray Slide Production

Approximately eighty antibodies for drug-metabolizing enzymes and proteins functionally related to the drug-metabolizing enzymes were selected for rat antibody microarray slide production (See, Table 1). UDP-glucunonosyl transferase antibody was produced by immunization of a rabbit with a synthetic human peptide. Cross-reactivity with rat UDP glucuronosyl transferase is not known. Western blot analysis with hepatic proteins obtained from untreated rats and rats treated with phenobarbital under non-denaturing conditions revealed that the antibody produced for the human protein recognized the rat form.

The antibody solutions with increasing concentration of 0 (PBS), 0.5, 5, 50 and 500 µg/ml were spotted (spotting volume, 1 nl) on both polyacrylamide (hydrogel)- and nitrocellulose (FAST)-based antibody chips at the Michigan Life Sciences Corridor (MLSC) Proteomics facility at Van Andel Institute using split pin technology.

The top block of antibodies with duplicate spotting for each concentration was repeated on the bottom block (thus, quadruplicate for each concentration). Anti-sera and ascites fluids were also spotted without isolation of IgG (Table 1). Higher protein levels of the anti-sera and ascites fluids compared with purified IgG protein levels were spotted to compensate for proteins other than IgG in the sera and ascites fluids.

Anti-Flag IgG (an internal control) (Sigma Co.), which recognized Flag protein (Sigma Co.) were also spotted in 0.5, 5, 50 and 500 µg/ml solutions in duplicate for three times in each block (top and bottom blocks). The peptide sequence of the internal control protein was not present in mammalian cells. The Flag internal control served as a landmark for orientation of the chip and as an internal control for probe labeling and hybridization efficiency. The normalization factor for each IgG concentration was obtained using the data obtained with three Flag proteins.

Example 2

Comparison of Spotting Efficiency of Antibodies on Polyacrylamide (Hydrogel)-Based Chips with that of Nitrocellulose (Fast)-Based Chips Both polyacrylamide (hydrogel)- and nitrocellulose (FAST)-based chips were produced with 0.5, 5, 50 and 500 µg/ml IgG concentration (1 nl per spot in duplicate on both top and bottom of the slide) and 0.5 and 1 mg/ml IgG concentrations (1 nl per spot in triplicate on both top and bottom of the slide) at the MLSC Proteomics facility at Van Andel Institute.

The chip was blocked for 45 minutes at room temperature with TTBS solution. A quality control analysis was carried out by hybridizing the chip with 25 µg Cy3-conjugated anti-rabbit IgG mixed with 50 µg Cy5-conjugated anti-mouse IgG (total volume, 1 ml) for one hour at room temperature. Washing was carried out with TTBS for four times. The chip was dried and imaging was carried out using GenePix4000A. Hybridization of the hydrogel chips with anti-mouse and anti-rabbit IgG showed fluorescent signal strength similar to the signal obtained with the FAST chip. Alternatively, the chip was hybridized with Cy3- or Cy5-conjugated secondary IgG (single dye experiment).

Example 3

Quality Control of Antibody Microarray Slides and Selection of Optimal Antibody Concentration for Spotting A hydrogel antibody chips with 05, 5, 50 and 500 µg/ml antibody concentrations (1 nl per spot) were produced at the MLSC Proteomics facility at Van Andel Institute. The chip was blocked for 45 minutes at room temperature with TTBS solution. A quality control analysis was carried out by hybridizing the chip with 25 µg Cy3-conjugated anti-rabbit IgG mixed with 50 µg Cy5-conjugated anti-mouse IgG (total volume, 1 ml) for one hour at room temperature. Washing was carried out with TTBS for four times. The chip was dried and imaging was carried out using GenePix 4000A.

As shown in FIG. 1, "Quality Control," majority of visible antibody spots was round and with even density. No background dye binding was detected. However, in both Cy3 and Cy5 spots, majority of 0.5 and 5 μg/ml antibody spots showed poor or no fluorescent signals whereas 50 and 500 μg/ml showed strong signals. The quality control analysis using secondary IgG revealed that the 0.5 μg/ml spots were under the detection limit (Table 2).

Example 4

Antibody Microarray Analysis of Phenobarbital (PB) Up-Regulated Proteins Using Rat Drug-Metabolizing Enzyme Chips Using the antibody chips (hydrogel) spotted with rat drug-metabolizing enzymes as shown in Table 1, microarray analyses were carried out with liver microsomes+cytosol obtained from 2 untreated (control) rat and 2 rats after treatment with phenobarbital (PB) (100 mg/kg/day for 3 days). Two sets of array analyses (control rat 1 vs. phenobarbital treated rat 1 and control rat 2 vs. phenobarbital-treated rat 2) were carried out using a direct design. Control and PB-treated protein samples were labeled with both Cy3 and Cy5 to be used for dye swapping.

The hydrogel chips were blocked overnight at 4° C. with 1% BSA/PBS blocking solution. The rat hepatic proteins were dialyzed with 10 kDa molecular cut-off membrane: An internal control protein, Met-Flag fusion proteins of *E. coli* bacterial alkaline phosphatase recognized by anti-Flag (Sigma Co.) was added to both untreated and PB-treated samples prior to Cy3 or Cy5 conjugation. The rat proteins (1 mg) with Flag protein (2 μg) were mixed and cross-linked with NHS-Cy3 or NHS-Cy5 (Amersham) (0.2 mg) according to the manufacturer's instructions. The probes were washed three times with 500 μl PBS and concentrated to 40 μl using microconcentrator spin columns (Amicon, 10 kDa cut-off). As described above for Control 1/PB 1 set (1st set) and Control 2/PB 2 set (2nd set), hybridization of the probes with dye swaps (in total, 4 hybridizations, 16 data points for each IgG concentration) was carried out for four hours at room temperature in Detroit R&D hybridization buffer (total volume, 750 μl). The hybridization solution contained 2 mg of rat liver protein. A representative image is shown in FIG. 1, "Experiment."

After hybridization, the chips were dried and images (4 images, 4 data points per image, in total, 16 data points) were scanned at 532 nm (green) and 635 nm (red) and pseudo-colored images were obtained using GenePix 4000A. A spot design (gal) file was produced from a spreadsheet to identify location of each protein in the 384-well plate. Signal intensity of each target protein was quantified with Genepix software using the gal file, which contained identity of each protein and its location in the 384-well plate. The GenePix data file was incorporated into GeneSpring microarray clustering and statistical analysis (Silicon Genetics).

Out of 312 (78 antibodies×4 concentrations) consolidated protein data points (76 proteins+2 additional Flag proteins with 4 various concentration of antibodies), 12 consolidated protein data points showed up-regulated expression levels that were same or higher than 2-fold after PB treatment (Table 3). They were identified as CYP2B1 (with 50 μg/ml spots), 30.6-fold; CYP2B1/2B2 (with 500 μg/ml spots), 9.7-fold; CYP 2B1 (with 500 μg/ml spots), 9.3-fold; mEH (with 5 μg/ml spots), 3.2-fold; mEH (with 50 μg/ml spots), 2.9-fold; CYP3A1/2/23 (with 50 μg/ml spots), 2.6-fold; calpain (with 5 μg/ml spots), 2.5-fold; calpain (with 50 μg/ml spots), 2.5-fold; COX-2 (with 500 μg/ml spots), 2.3-fold; 20 (with 500 μg/ml spots), 2.1-fold; CYP3A1/2/23 (with 500 μg/ml spots), 2.1-fold; and COX-2 (with 50 μg/ml spots), 2.0-fold. Majority of 0.5 and 5 μg/ml antibody spots failed to show signal levels higher than 10 for both control and PB treated samples.

GeneSpring analysis of 500 μg/ml antibody spots is shown in FIG. 2. The middle diagonal line is for a protein expression level that did not change after PB treatment, the top line is for 2-fold increase and the bottom line is for 2-fold decrease. Internal control, Flag proteins (3 sets) (2 μg), spiked to 1 mg of sample, was close to the middle line and showed high signal values (mean value, 2663). GST-alpha and antioxidant-like protein 1 also showed high expression levels without any change. CYP2B1 and CYP2B1/2B2 spots were above the 2-fold increase line with 9.3- and 9.7-fold increase, respectively, after PB treatment. CYP2B1 has been reported to be the primary protein that increases after PB treatment.

An interesting observation is that CYP2B1 protein bound to both CYP2B1 IgG and CYP2B1/2B2 IgG. All data obtained from 500 μg/ml antibody spots produced signals higher than 20 in both control and PB-treated samples except for iNOS, prostaglandin $E_2$ synthase, CYP2E1, IRP-1 and Guanylyl Cyclase beta 1. Polyclonal anti-serum for human CYP3A4 were produced and characterized to be specific for rat CYP3A (CYP3A1, 3A2 and 3A23). The CYP3A antibody spotted on the chip showed strong signals (2.6- and 2.1-fold increase after PB treatment with 50 and 500 μg/ml IgG spots, respectively). CYP3A has also been reported to be a protein, which increases after PB treatment.

In addition to the antibody for CYP3A, additional polyclonal antibodies as a form of IgG or anti-sera were spotted for this chip (Table 1). Further, 6 mouse ascites fluids including antibodies for tubulin-alpha (1.7-fold increase after PB treatment), alpha-actin (0.8-fold of control, 20% decrease) and beta actin (1.6-fold increase) were also successfully used for antibody array production (Tables 1 and 4). This result demonstrated that anti-sera or ascites (without immunoglobulin purification, thus containing high levels of proteins) could be spotted on the chip for a successful antibody microarray analysis.

Example 5

Normalization of Microarray Data using Internal Control Molecules Spiked to Protein Prior to Dye Conjugation Anti-Flag IgG, an internal control protein for Cy3 and Cy5 conjugation and hybridization, was spotted in 0.5, 5, 50 and 500 μg/ml solutions in duplicate for three times in each block (top and bottom blocks). Thus, each concentration has 16 data points (8 data points from Control 1/PB 1 and 8 data points from Control 2/PB 2) of three sets. The fold increase of the three sets of Flag proteins was 1.0-, 1.0- and 0.9-fold (mean, 1.0) with 500 μg/ml spots and 1.2-, 0.9- and 0.8-fold (mean, 0.97) in 50 μg/ml IgG spotting. An interesting observation is that signal levels of the three Flag proteins were somewhat different among the three sets, especially with 50 μg/ml spots. Nonetheless, ratios obtained by direct competition of Cy3- or Cy5-conjugated control with Cy5- or Cy3-conjugated PB treated samples were very similar. This was due to variation in antibodies levels spotted on a chip. This result demonstrated that, with 2 fluors directly competing for a spot, a slight variation in spotting efficiency did not affect the outcome of a successful array analysis. At 0.5 and 5 μg/ml anti-Flag IgG spots, the majority of dye signals were lower than 10 in both Cy3 and Cy5 conjugated samples.

House-keeping protein expression was varied from 0.7- to 1.7-fold increase after PB treatment (Table 4). According to this data in Table 4, G3PDH (no change) was selected to be used for normalization of cytosolic protein expression analyzed by Western blot analysis. Increased protein expression of tubulin-alpha (1.7-fold) and beta actin (1.6-fold), which are widely used as an internal control for Western blot analysis, was unexpected.

Example 6

Verification of Microarray Analysis

Protein levels of CYP2B1/2B2, CYP2B1, CYP3A1/2/23, COX-2 and CYP2D6 increased after PB treatment as seen in the results obtained from array analyses with 500 mg/ml IgG spots (Table 5). This microarray result was obtained by combining results from Control 1 and PB 1 assays and Control 2 and PB 2 assays. Expression levels of CYP2B1/2B2, CYP2B1, COX-2, CYP2D, CYP3A1/2/23, CYP2C11 and G3PDH in Rat #1 (Control 1), Rat #2 (PB 1), Rat #3 (Control 2) and Rat #4 (PB 2) were verified by Western blot analyses of microsomal and cytosolic proteins. Protein bands obtained by Western blot analyses were quantitated using a densitometer (Molecular Dynamics). Levels of microsomal proteins, CYP2B1/2B2, CYP2B1, CYP2D, and CYP3A, were normalized by microsomal CYP2C11 levels, which did not change after PB treatment. COX-2 expression usually detected in microsomes also detected in cytosol. The cytosolic COX-2 levels were normalized by G3PDH levels. Comparison of up-regulated expression obtained by array analyses with Western blot analysis is shown in Table 5. There was agreement in results obtained by the arrays with Western blot analyses except for CYP2D expression levels, which increased by array analysis, but failed to increase by Western blot analysis. Increased levels of microsomal epoxide hydrolase and calpain after PB treatment (Table 3) were also verified by Western blot analysis.

Example 7

Intense Molecular Signal Conjugation

A conjugation method was developed so that majority of $NH_2$ and $NH_3^+$ groups present in proteins were occupied with conjugated Cy3 and Cy5 molecules. Intense labeling of the proteins was verified using PAGE analysis followed by Coomassie blue staining. Anti-mouse IgG with minimal Cy5-conjugation and proteins without conjugated dye molecules stained in blue whereas Cy3- and Cy5-conjugated proteins showed pink (visible color of Cy3) and bluish green (visible color of Cy5) bands (FIG. 3, top). Intense labeling of the protein prevented recognition of microsomal epoxide hydrolase by the antibodies (FIG. 3, bottom). This is due to interference of the dye molecule conjugated to the epitope of the protein recognized by the IgG. Thus, this method cannot be used for Cy3 and Cy5 conjugation of sample proteins or protein detection molecules (streptavidin or anti-digoxigenin), which have to be recognized by IgG and bind biotin or digoxigenin, respectively. However, the method can be utilized to attach the intensely labeled proteins (Intense Molecular Signals) via carboxyl groups of the molecules to proteins (direct array analysis), streptavidin or anti-digoxigenin (indirect array analysis). This method increases signal intensity without sacrificing interactions between IgG and protein or between biotinylated or digoxigenin-bound protein and streptavidin or anti-digoxigenin

TABLE 1

A list of antibodies spotted for rat drug-metabolizing enzyme microarrays.

| P450 Phase I Drug-Metabolizing Enzyme | Phase II Drug-Metabolizing Enzyme |
|---|---|
| 1A1 (M/IgG)[b] | N-acetyltransferase form-I (P/S)[d] |
| 1A1/1A2 (M/IgG)[b] | N-acetyltransferase form-I (P/S)[d] |
| 2A (P/S)[d] | GST-alpha (P/IgG)[c] |
| 3A1 (M/IgG)[b] | GST-mu (P/IgG)[c] |
| 3A2 (M/IgG)[b] | GST-pi (P/IgG)[c] |
| 3A23 (P/S)[d] | Microsomal Epoxide Hydrolase (P/S)[d] |
| 3A1/3A2/3A23[a] (P/S)[d] | UDP-Glucuronosyltransferase (P/S)[d] |
| 4A2 (P/S)[d] | Anti-Oxidant Protein |
| 1B1 (P/S)[d] | Superoxide Dismutase (P/IgG)[c] |
| 2B1 (M/IgG)[b] | Catalase (P/S)[d] |
| 2B1/2B2 (M/IgG)[b] | Glutathione Peroxidase (P/IgG)[c] |
| 2C11 (M/IgG)[b] | House Keeping Protein |
| 2C23 (P/IgG)[c] | Tubulin-alpha (A/CM)[e], Tubulin-beta (M/IgG)[b] |
| 2D (P/S)[d] | Beta-Actin (A/CM)[e] |
| 2E1 (P/IgG)[c] | G3PDH (M/IgG)[b] |
| 2G1 (P/IgG)[c] | Alpha-Actin (A/CM) |
| 2J3/2J4 (P/IgG)[c] | IRP-1 (P/IgG)[c] |
| Co-Enzyme for CYP Activity | Oxidative Stress Protein |
| Cytochrome b5 (P/S)[d] | sPLA2 (P/IgG)[c] |
| P450-NADPH-Reductase (P/S)[d] | iNO Synthase (P/IgG)[c] |
| Additional Phase I Drug-Metabolizing Enzyme | nNOSynthase (P/IgG)[c] |
| Carboxylesterase (P/S)[d] | eNOSynthase (P/S)[d] |
| Mitochondrial Protein | COX-1 (P/IgG)[c] |
| Bax (M/IgG)[b] | COX-2 (P/S)[d] |
| Bcl-2 (M/IgG)[b] | 5-Lipoxygenase (P/S)[d] |
| Cytochrome C (M/IgG)[b] | Thromboxane (P/IgG)[c] |
| PBR (p/S)[d] | ProstaglandinE Synthase (P/IgG)[c] |
| Apoptosis-Related Protein | Calpain (P/S)[d] |
| Apaf1 (P/IgG)[c] | NFkapaB (P/S)[d] |
| Bad (P/IgG)[c] | PPAR (Peroxisome Proliferator-Activated Receptors)-Alpha (P/IgG)[c] |
| Bak (M/IgG)[b] | P-Glycoprotein (P-gp) (A/CM)[e] |
| BID (P/S)[d] | TNF-alpha (P/IgG)[c] |
| Caspase3 (P/S)[d] | Heme Oxygenase-1 (P/IgG)[c] |
| Caspase8 (P/IgG)[c] | Heme Oxygenase-2 (P/IgG)[c] |
| Caspase10 (P/IgG)[c] | Guanylyl Cyclase a1 (P/IgG)[c] |
| FADD (P/IgG)[c] | Guanylyl Cyclase b1 (P/IgG)[c] |
| Fas (P/IgG)[c] | Beta Catenin (P/S)[d] |
| p53 (M/IgG)[b] | CEA(Carcinoembryonic Antigen) (A/CM)[e] |
| PARP (M/IgG)[b] | Antioxidant-like Protein 1 (M/IgG)[b] |
| TRAIL (P/IgG)[c] | Intracellular Protein Degradation Protein |
| Rb (M/IgG)[b] | Calpastatin (A/CM)[e] |
| Internal Control | E1 Ubiquitin (P/IgG)[c] |
| Flag (M/IgG)[b] | |

[a]Anti-CYP3A4 which is specific for CYP3A subfamily.
[b]Monoclonal IgG: M/IgG
[c]Polyclonal IgG: P/IgG
[d]Polyclonal Anti-Serum: P/S
[e]Mouse Ascites Fluid or Cell Culture Media: A/CM

TABLE 2

IgG concentration-dependent visible spots obtained after hybridizaion of drug metabolizing enzyme slides with secondary anti-mouse and anti-rabbit IgG. The image of the slide is shown in FIG. 1, "Quality Control". Antibodies for the array were spotted in 4 blocks (2 spots in each concentration) in top and 4 repeating blocks in bottom. Spots in block 1 (144 spots) were used for % visible spot counting.

| IgG concentration (µg/ml) | % Visible Spot | % Not Visible Spot |
|---|---|---|
| 500 | 100 | 0 |
| 50 | 89 | 11 |
| 5 | 28 | 72 |
| 0.5 | 0 | 100 |

TABLE 3

Fold-change of expression levels of proteins after phenobarbital (PB) treatment of rats: Number of proteins up-regulated higher than 2-fold obtained from microarray analyses was 0 out of 75 proteins at 0.5 μg/ml IgG spots, 2 out of 75 proteins at 5 μg/ml IgG spots, 5 out of 75 proteins at 50 μg/ml IgG spots and 5 out of 75 proteins at 500 μg/ml IgG spots.

| Protein | Fold-Change of Protein Expression Level after PB treatment | | | |
|---|---|---|---|---|
| | 0.5 μg/ml IgG | 5 μg/ml IgG | 50 μg/ml IgG | 500 μg/ml IgG |
| Up-Regulated Proteins | | | | |
| CYP2B1 (monoclonal IgG) | | | 30.6[a] | 9.3[a] |
| CYP2B1/2B2 (monoclonal IgG) | | | | 9.7 |
| MEH (polyclonal anti-serum) | | 5.2 | 2.9 | |
| CYP3A (polyclonal anti-serum) | | | 2.6 | 2.1 |
| Calpain (polyclonal anti-serum) | | 2.5 | 2.5 | |
| COX-2 (monoclonal IgG) | | | 2.0 | 2.3 |
| CYP2D Internal Control | | | | 2.1 |
| Flag #1 | ND[b] | ND[b] | 1.2 | 1.0 |
| Flag #2 | | | 0.9 | 1.0 |
| Flag #3 | | | 0.8 | 0.9 |

[a]From 16 data points obtained from two sets of experiments with dye swaps: the first set (8 data points) is from control rat #1 and PB treated rat #3, and the second set is from control rat #2 and PB treated rat #4.
[b]Signal strength is under 10 (arbitrary unit).

TABLE 4

Fold-change of protein expression levels of house-keeping proteins after phenobarbital (PB) treatment of rats: Flag internal control protein was spiked to hepatic proteins obtained from untreated or PB treated rats.

| Proteins Level | Fold-Change of Protein Expression |
|---|---|
| House-keeping Proteins | |
| Tubulin-alpha | 1.7[a] |
| Beta-actin | 1.6 |
| G3PDH | 1.0 |
| Alpha-actin | 0.8 |
| Tubulin-beta Internal Control | 0.7 |
| Flag #1 | 1.0 |
| Flag #2 | 1.0 |
| Flag #3 | 0.9 |

[a]From 16 data points obtained from two sets of experiments with 500 μg/ml IgG with dye swaps: the first set (8 data points) is from control rat #01 and PB treated rat #3, and the second set is from control rat #2 and PB treated rat #4.

TABLE 5

Comparison of fold-increase of protein expression level obtained by antibody microarray versus Western blot analysis.

| Protein | Antibody Microarray | Western Blot Analysis |
|---|---|---|
| Up-Regulated Proteins | | |
| CYP2B1/2B2 | 9.70[a] | Highly Induced[b] |
| CYP2B1 | 9.30 | Highly Induced[b] |
| COX-2 | 2.30 | Moderately Induced[c] |
| CYP2D | 2.10 | 1.07 ± 0.61[d] |
| CYP3A | 2.10 | 7.00 ± 4.80[d] |
| House-Keeping Proteins | | |
| G3PDH Internal Control | 1.00 | 1.00 |
| Flag #1 | 1.10 | |
| Flag #2 | 1.10 | |
| Flag #3 | 0.90 | |

[a]From 16 data points obtained from two sets of experiments with dye swaps: the first set (8 data points) is from control rat #1 and PB treated rat #3, and the second set is from control rat #2 and PB treated rat #4.
[b]Not detected in control but strong band after PB treatment.
[c]Not detected in control but bands with a medium intensity detected after PB treatment.
[d]Quantitation of Western blot analysis data obtained from two sets of experiments normalized by G3PDH expression. The mean value and difference of each data from the mean value are shown.

Throughout this application, various publications, including United States patents, are referenced by author and year and patents by number. Full citations for the publications are listed below. The disclosures of these publications and patents in their entireties are hereby incorporated by reference into this application in order to more fully describe the state of the art to which this invention pertains. The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the described invention, the invention can be practiced otherwise than as specifically described.

REFERENCES

Haab, B. B., Dunham, M. J., Brown, P. O. Protein microarrays for highly parallel detection and quantitation of specific proteins and antibodies in complex solutions. Genome Biol. 2, research 0004.1-0004.12 (2001).

Leukling, A., Horn, M., Eickhoff, H., Bussow, K., Lehrach H. and Walter, G., "Protein microarrays for gene expression and antibody screening." Anal. Biochem. 270, 103-111 (1999).

MacBeath, G. and Schreiber, S. L. Printing proteins as microarrays for high-throughput function determination. Science 289, 1760-1763 (2000).

Miller, J. C., Zhou, H., Kwekel, J., Cavallo, R., Burke, J., Butler, E. B., The, B. S. and Haab, B. B. Antibody microarray profiling of human prostate cancer sera: Antibody screening and identification of potential biomarkers. Proteomics 3, 56-63 (2003).

Streekumar, A., Nyati, M. K., Varambally, S., Barrette, T. R., Ghosh, D., Lawrence, T. S. and Chinnaiyan, A. M. Profiling of cancer cells using protein microarrays: Discovery of novel radiation-regulated proteins. Cancer Res. 61, 7585-7593 (2001).

Zhou, H., Bouwman, K., Schotanus, M., Verweij, C., Marrero, J. A., Dillon, D, Costa, J., Lizardi, P., and Haab, B., "Two color, rolling circle amplification on antibody microarrays for sensitive, multiplexed serum protein measurements," Genome Biology, 5:R28, (2004).

What is claimed is:

1. An antibody microarray screening method including the steps of:
   depositing either a plurality of spots including at least one spot deposited as an unpurified antibody solution, or a plurality of spots including at least one spot deposited as an unpurified antibody solution and at least one spot deposited as a purified antibody solution, on predetermined positions on a substrate;
   hybridizing the plurality of spots with a plurality of labeled target proteins;
   quantifying the label signal strength produced at each spot;
   quantifying levels of target protein captured at each spot on the basis of label signal strength; and
   comparing levels of target protein among the plurality of samples of labeled target proteins.

2. The antibody microarray screening method according to claim 1, wherein the antibodies are specific for proteins selected from the group consisting of drug-metabolizing enzymes and proteins functionally related with said drug-metabolizing enzymes.

3. The antibody microarray screening method according to claim 2, wherein the antibodies specific for drug-metabolizing enzymes are antibodies specific for cytochromes P450.

4. The antibody microarray screening method according to claim 2, wherein the antibodies specific for proteins functionally related with said drug-metabolizing enzymes are antibodies specific for at least one protein selected from the group consisting of mitochondrial proteins, apoptosis-related proteins, anti-oxidant proteins, oxidative stress proteins, and intracellular protein degradation proteins.

5. The antibody microarray screening method according to claim 1, wherein the substrate is polyacrylamide-based hydrogel coating.

6. The antibody microarray screening method according to claim 1, further including the step of determining an optimal dilution factor for the unpurified antibody solution and an optimal concentration for the purified antibody solution, the step further including the steps of:
   depositing, at a first set of locations, a plurality of spots of the purified antibody solution, each of the spots of the purified antibody solution comprising one of a plurality of antibody concentrations;
   depositing, at a second set of locations, a plurality of spots of the unpurified antibody solution, each of the spots of the unpurified antibody solution comprising one of a plurality of dilution factors;
   hybridizing the spots of the purified antibody solution and the spots of the unpurified antibody solution with labeled secondary immunoglobulins;
   scanning and quantifying the signal strength of label at each of the spots;
   selecting an optimal concentration of the purified antibody solution on the basis of the production of an optimal label signal strength; and
   selecting an optimal dilution factor of the unpurified antibody solution by selecting a dilution factor that yields a label signal strength similar to that produced by the optimal concentration of the antibody solution.

7. The antibody microarray screening method according to claim 1, wherein the unpurified antibody solution is selected from the group consisting of an ascites fluid, a hybridoma culture medium, and an antiserum.

8. The antibody microarray screening method according to claim 6, wherein the step of scanning and quantifying the signal strength of label at each of the spots is further defined as scanning and determining the percentage of visible spots in a scanned image.

9. The antibody microarray screening method according to claim 1 wherein the step of depositing either a plurality of spots including at least one spot deposited as an unpurified antibody solution or a plurality of spots including at least one spot deposited as an unpurified antibody solution and at least one spot deposited as a purified antibody solution, is further defined as depositing the unpurified antibody solution at a higher amount of protein than the purified antibody solution, thereby compensating for the lower concentration of antigen specific immunoglobulins in the unpurified antibody solution.

10. The antibody microarray screening method according to claim 9, wherein the step of depositing either a plurality of spots including at least one spot deposited as an unpurified antibody solution or a plurality of spots including at least one spot deposited as an unpurified antibody solution and at least one spot deposited as a purified antibody solution is further defined as depositing the unpurified antibody solution at a 10-fold and/or 100-fold dilution, and depositing the purified antibody solution at a protein concentration of greater than 5 µg/ml.

* * * * *